United States Patent [19]

Chenard

[11] Patent Number: 4,571,404

[45] Date of Patent: Feb. 18, 1986

[54] SUBSTITUTED BENZOPENTATHIEPINS

[75] Inventor: Bertrand L. Chenard, Wilmington, Del.

[73] Assignee: E. I. Du Pont de Nemours and Company, Wilmington, Del.

[21] Appl. No.: 618,445

[22] Filed: Jun. 7, 1984

Related U.S. Application Data

[63] Continuation-in-part of Ser. No. 502,231, Jun. 8, 1983, abandoned.

[51] Int. Cl.[4] .................... C07D 341/00; A01N 43/24
[52] U.S. Cl. ........................................ 514/431; 549/11
[58] Field of Search ............... 549/11; 514/431; 71/90

[56] References Cited

U.S. PATENT DOCUMENTS 4,094,985  6/1978  Vladuchick .................... 424/270
4,275,073  6/1981  Moberg ........................ 424/273 P

OTHER PUBLICATIONS

Chenard et al., *J. Org. Chem.*, 49, 1221 (1984).
Feher et al., *Z. Anorg. Allg. Chem.*, 452, 37 to 42 (1979).
Feher et al., *Tet. Lett.*, 2125 to 2126 (1971).
Feher et al., *Z. Naturforsch.* B, 27, 1006 (1972).
Feher et al., *Angew. Chem. Int. Ed.*, 6, 703 (1967).
Nametkin et al., in *Izv. Akad. Nauk. SSSR*, Ser. Khim. 12, 2841 (1980).
Watkins et al., *J. Het. Chem.*, 19 459 to 462 (1982).
Kurzer in "Org. Compd. of Sulphur, Selenium, Tellurium", Royal Society of Chemistry, London, vols. 1 to 6 (1970 to 1980).
Oae, "Organic Chemistry of Sulfur" at pages 346 to 348, Plenum Press, N.Y. (1977).
Cairns et al., *J. Am. Chem. Soc.*, 74, 3982 to 3989 (1952).
Hunig et al., *Liebigs Ann. Chem.*, 738, 192 to 194 (1970).

*Primary Examiner*—Robert Gerstl
*Attorney, Agent, or Firm*—James A. Costello

[57] ABSTRACT

Substituted benzopentathiepins, their preparation from 1,2,3-benzothiadiazoles and elemental sulfur, selected 1,2,3-benzothiadiazoles; the benzopentathiepins being useful as biologically active compounds or as intermediates to 1,2-benzenedithiols.

20 Claims, No Drawings

SUBSTITUTED BENZOPENTATHIEPINS

CROSS-REFERENCE TO RELATED APPLICATION

This is a continuation-in-part of copending application Ser. No. 502,231 filed on June 8, 1983 now abandoned.

BACKGROUND OF THE INVENTION

This invention concerns substituted benzopentathiepins, intermediate 1,2,3-benzothiadiazoles and the process for making the former by reacting the latter with elemental sulfur.

Unsubstituted benzopentathiepin is known (Feher et al., *Z. Anorg. Allg. Chem.*, 452, 37 to 42 (1979); Feher et al., *Tet. Lett.*, 2125 to 2126 (1971). It is prepared from 1,2-benzenedithiol and $S_3Cl_2$. No utility is described. Feher et al., in *Z. Naturforsch. B*, 27, 1006 (1972), describe preparation of the 7,8-dimethyl derivative by a similar method.

A reduced hexahydrobenzopentathiepin was prepared by Feher et al., according to the method of Feher et al. described above: *Angew. Chem. Int. Ed.*, 6, 703 (1967). Nametkin et al., in *Izv. Akad. Nauk. SSSR, Ser. Khim.*, 12, 2841 (1980), describe a method for making said reduced pentathiepins by use of an organoiron complex.

Watkins et al., *J. Het. Chem.*, 19, 459 to 462 (1982) describe the x-ray crystal structure of a complex indene pentathiepin. Synthesis and utility are not described.

A variety of heterocyclic pentathiepins are known. For instance, U.S. Pat. No. 4,094,985 describes the following as fungicides:

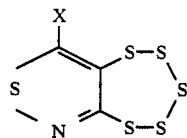

where X is CN or

et cetera. U.S. Pat. No. 4,275,073 describes these pyrazolopentathiepins as fungicides:

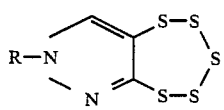

where R=H, $C_1$-$C_6$ alkyl, $C_5$-$C_6$ cycloalkyl, —$CH_2\phi$, —Ar. Both of the patents describe processes employing a thiol or dithiol and $S_2Cl_2$. The substituted benzopentathiepins of this invention cannot be made by literature techniques.

Certain 1,2,3-benzothiadiazoles are known, their syntheses being reviewed by Kurzer in "Org. Cmpd. of Sulphur, Selenium, Tellurium", Royal Society of Chemistry, London, Vols. 1 to 6 (1970 to 1980). A typical synthesis is diazotization of an o-aminobenzenethiol as follows:

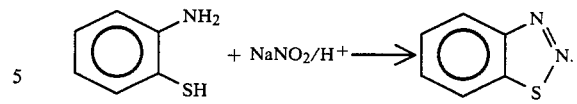

In Oae, "Organic Chemistry of Sulfur", at pages 346 to 348, Plenum Press, N.Y. (1977), are reviewed the various means for reducing disulfides to give thiols. Reagents for these reductions include sodium borohydride, lithium aluminum hydride, sodium amalgam, zinc or tin with aqueous acid, phosphines and phosphites.

Cairns et al., *J. Am. Chem. Soc.*, 74, 3982 to 3989 (1952), describe the reduction of a linear tetrasulfide by lithium aluminum hydride. There is no known art, however, that describes reduction of a pentathiepin to give a dithiol.

The 1,2-benzenedithiols can be prepared by pyrolysis of benzothiadiazoles in the presence of carbon disulfide and alkaline hydrolysis of the intermediate trithiocarbonate: Hunig et al., *Liebigs Ann. Chem.*, 738, 192 to 194 (1970). The process requires a pressure vessel and temperatures of 220° C.

SUMMARY OF THE INVENTION

This invention concerns novel substituted benzopentathiepins of the formula:

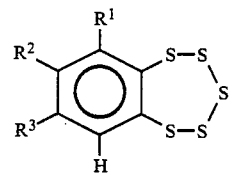

wherein
$R^1$, $R^2$ and $R^3$ are the same or different substituents that do not react with sulfur at elevated temperatures and are selected from H (no more than two of $R^1$, $R^2$ and $R^3$ being H), X, $CX_3$, $NO_2$, $SR^4$, $OR^4$, $NR_2^4$,

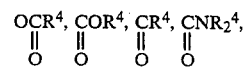

aryl and substituted aryl;
$R^4$ is selected from aryl, substituted aryl and substituted and unsubstituted branched or straight chain $C_1$ to $C_6$ alkyl; and
X is selected from Cl, Br and F.

The primary requirement of the $R^1$, $R^2$ and $R^3$ substituents is that they be substantially unreactive with sulfur at reaction temperatures. Several groups of such substituents are given as examples with no intent that the invention be limited thereto.

The substituents on substituted $R^4$ aryl and alkyl groups are selected from X, $CX_3$, OR, SR,

and COOR, wherein R is aryl or $C_1$ to $C_4$ straight or branched alkyl. Preferred benzopentathiepins of this invention are those wherein: (1) $R^1$ and $R^3$ are both H and $R^2$ is selected from X, $CX_3$, $SR^4$, $OR^4$, $NR_2^4$, $COOR^4$, aryl and substituted aryl; (2) $R^2$ and $R^3$ are both H and $R^1$ is selected from X, $CX_3$, $SR^4$, $OR^4$, $NR_2^4$, $COOR^4$, aryl and substituted aryl; and (3) $R^1$ and $R^2$ are both $NR_2^4$ and $R^3$ is H. Especially preferred compounds are those in category (1) wherein $R^2$ is $N(CH_3)_2$, $OCH_3$, $CF_3$ or Cl; those in category (2) wherein $R^1$ is $CF_3$ or Br; and the compound in category (3) wherein $R^4$ is methyl. The latter compound is named 6,7 bis(dimethylamino)benzopentathiepin.

This invention also concerns the method for making benzopentathiepins by the following reaction:

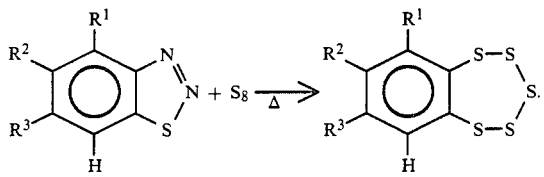

The reaction is typically carried out in an inert solvent at temperatures between about 140° to 200° C., with about 160° to 190° C. being preferred. The $R^1$, $R^2$ and $R^3$ substituents are as defined heretofore except that the novel process also includes the making of compounds wherein $R^1 = R^2 = R^3 = H$.

Suitable solvents are those which are inert to elemental sulfur and are tolerant of temperature and pressure combinations required to meet the temperature range described. The solvents include but are not limited to decahydronaphthalene, nitrobenzene, dichlorobenzenes, dimethylformamide and dimethyl sulfoxide. The reaction is normally carried out in an inert atmosphere such as nitrogen, argon, helium and the like. The molar ratio of elemental sulfur (calculated as $S_8$) to benzothiadiazole can range from about 1:2 to 2:1; the preferred ratio is about 1:1.

This invention also concerns the method for making said benzopentathiepins in the presence of 1,4-diazabicyclo[2.2.2]octane (DABCO):

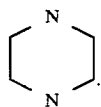

The molar ratio of DABCO to benzothiadiazole is about 0.1:1 to 2:1; the preferred ratio is about 1:1. Employing DABCO in the process of the invention has been found to increase product yields substantially.

This invention also concerns these novel benzothiadiazoles:

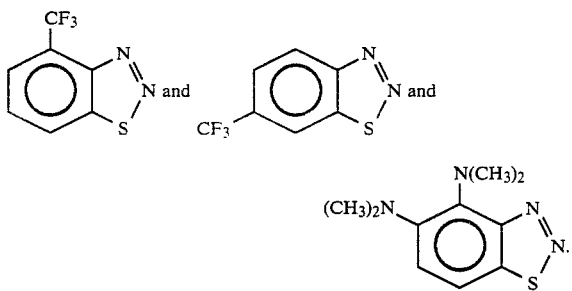

This invention also concerns the method for making substituted 1,2-benzenedithiols by reduction of benzopentathiepins according to the reaction:

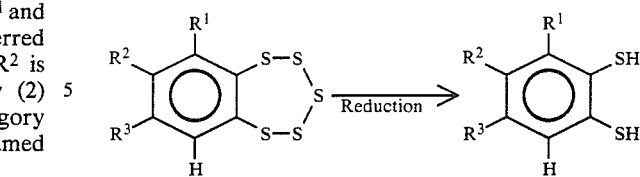

wherein $R^1$, $R^2$ and $R^3$ are as defined above including $R^1 = R^2 = R^3 = H$.

Suitable reducing agents for said process include but are not limited to sodium borohydride, lithium aluminum hydride, trialkyl phosphites, zinc/aqueous acid, and the like. Sodium borohydride and lithium aluminum hydride are preferred. The reaction temperature can be about 0° to 60° C.; the preferred range for sodium borohydride, for reasons of ease of reactivity, is about 20° to 40° C.; the preferred range for lithium aluminum hydride is about 0° to 35° C.

DETAILS OF THE INVENTION

In the matter of making 1,2-benzenedithiols, the following information will guide one skilled in the art regarding choice of solvents. The process employing sodium borohydride is run with a protic solvent, with or without non-protic solvents as diluent. Solvents suitable for the sodium borohydride process include but are not limited to methanol, ethanol, isopropanol, butanol and water. Non-protic diluents include tetrahydrofuran. Other solvents can be selected empirically depending on the type of reducing agent selected. Thus, lithium aluminum hydride requires non-protic solvents such as diethyl ether or tetrahydrofuran.

The molar ratio of sodium borohydride or lithium aluminum hydride to benzopentathiepin can range from about 2:1 to 6:1; a ratio of about 4:1 is preferred. The process employing lithium aluminum hydride should be run in the absence of water. The reaction process initially gives a dithiolate salt which can be further reacted with aqueous acid to give the 1,2-benzenedithiols, or with alkylating agents such as methyl iodide to give di-thioethers.

The second choice gives materials which are protected against aerobic oxidation.

An additional aspect of this invention concerns the use of selected benzopentathiepins as anti-fungal and anti-viral agents. For example, the compounds of Table 1 were found to be effective against the recited fungus and virus types. Details concerning formulations and control methodology follow the Table.

TABLE 1

| Compound | Fungus or Virus[1] | Rate | % Control |
|---|---|---|---|
| 7-Trifluoromethyl- | AS | 100 ppm | 100 |
| benzopentathiepin | RB | 100 ppm | 90 |
| 7-Dimethylamino- | AS | 100 ppm | 100 |
| benzopentathiepin | CPM | 100 ppm | 100 |
|  | CMV | 100 ppm | 100 |
|  | BPM | 100 ppm | 55 |
| 7-Methoxybenzo- | AS | 100 ppm | 100 |
| pentathiepin | CPM | 100 ppm | 93 |
|  | BPM | 100 ppm | 95 |
| 6-Trifluoromethyl benzopentathiepin | CPM | 100 ppm | 100 |
| 6,7-bis(dimethylamino)- | AS | 100 ppm | 80 (primary) |
| benzopentathiepin |  |  | 98 (confirmatory) |
|  | WLR | 100 ppm | 80 (primary) |

TABLE 1-continued

| Compound | Fungus or Virus[1] | Rate | % Control |
|---|---|---|---|
| | | | 57 (confirmatory) |

[1]AS = apple scab
RB = rice blast
CPM = cucumber powdery mildew
BPM = barley powdery mildew
CMV = cucumber mosaic virus≠WLR = wheat leaf rust

PLANT DISEASE CONTROL FORMULATIONS

Useful formulations of benzopentathiepins can be prepared in conventional ways. They include dusts, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions can be used primarily as concentrates which are to be diluted prior to ultimate use. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the approximate proportions set forth in Table 2 with the active ingredients plus at least one surfactant or diluent being equal to 100 weight percent.

TABLE 2

| | Weight Percent | | |
|---|---|---|---|
| | Active Ingredient | Diluent(s) | Surfactant(s) |
| Wettable Powders | 20–90 | 0–74 | 1–10 |
| Oil Suspensions, Solutions Emulsions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| High Strength Compositions | 90–99 | 0–10 | 0–2 |

Lower or higher levels of active ingredient can be present, depending on the intended use and the physical properties of the compound. Higher ratios of surfactant to active ingredient are sometimes desirable and are achieved by incorporation into the formulation, or by tank mixing.

Some typical solid diluents are described in Watkins et al., "Handbook of Insecticide Dust Diluents and Carriers", 2nd Ed., Dorland Books, Caldwell, N.J. but other solids, either mined or manufactured, can be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, and the like.

Agricultural formulations that contain the compounds of this invention as active ingredient can also contain other active ingredients. The additional agricultural chemicals are employed in mixtures or combinations in amounts ranging from 0.05 to 25 parts by weight for each part by weight of the compound or compounds of this invention. The proper choice of amounts is readily made by one skilled in the art of protecting plants from pests. The following are illustrative of the agricultural chemicals that can be included in compositions or added to sprays containing one or more of the active compounds of this invention:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalimide (captan)
N-trichloromethylthiophthalimide (folpet)
dimethyl 4,4'-(o-phenylene)bis(2-thioallophanate) (thiophanate-methyl)
2-(thiazol-4-yl)benzimidazole (thiabendazole)
aluminum tris(O-ethyl phosphonate) (Aliette ®)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[(1,1,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)

Bactericides tribasic copper sulfate
streptomycin sulfate
oxytetracycline

Acaricides senecioic acid, ester with 2-sec-butyl-4,6-dinitrophenol (binapacryl)
6-methyl-1,3-dithiolo[2,3-B]quinonolin-2-one (oxythioquinox)
2,2,2-trichloro-1,1-bis(4-chlorophenyl)ethanol (dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)

Nematicides

2-[diethoxyphosphinylimino]-1,3-dithietane (fosthietan)
S-methyl-1-(dimethylcarbamoyl)-N-(methylcarbamoyloxy)thioformimidate (oxamoyl)
S-methyl-1-carbamoyl-N-(methylcarbamoyloxy)thioformimidate
N-isopropylphosphoramidic acid, O-ethyl-O'-[4-(methylthio)-m-tolyl]diester (fenamiphos)

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O,-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl N-[[(methylamino)carbonyl]oxy]ethanimidothioate (methomyl)
N'-(4-chloro-o-tolyl)-N,N-dimethylformamidine (chloridimeform)
O,O-diethyl-O-(2-isopropyl-4-methyl-6-pyrimidyl)-phosphorothioate (diazinon)
octachlorocamphene (toxaphene)
O-ethyl O-p-nitrophenyl phenylphosphononthioate (EPN)
cyano(3-phenoxyphenyl)-methyl 4-chloro-α-(1-methylethyl)benzeneacetate (fenvalerate)
(3-phenoxyphenyl)methyl (+)-cis,trans-3-(2,2-dichloroethenyl)-2,2-dimethylcyclopropanecarboxylate (permethrin)
dimethyl N,N'-[thiobis[(N-methylimino)carbonyloxy]]-bis[ethanimidothioate] (thiodicarb)
phosphorothiolothionic acid,
O-ethyl-O-[4-(methylthio)phenyl]-S-n-propyl ester (sulprofos)
α-cyano-3-phenoxybenzyl[3-(2,2-dichlorovinyl)-2,2-dimethylcyclopropane]carboxylate (cypermethrin)
cyano(3-phenoxyphenyl)methyl 4-(difluoromethoxy-α-(methylethyl)benzeneacetate (Payoff®)
O,O-diethyl-O-(3,5,6-trichloro-2-pyridyl)phosphorothioate (chlorpyrifos)
O,O-dimethyl-S-[(4-oxo-1,2,3-benzotriazin-3-(4H)-yl)-methyl]phosphorodithioate (azinphos-methyl)
5,6-dimethyl-2-dimethylamino-4-pyrimidinyl dimethyl carbamate (Pirimor®)
S-(N-formyl-N-methylcarbamoylmethyl)-O,O-dimethyl phosphorodithioate (formothion)
S-2-(ethylthioethyl)-O,O-dimethyl phosphiorothioate (demeton-S-methyl)
α-cyano-3-phenoxybenzyl cis-3-(2,2-dibromovinyl)-2,2-dimethylcyclopropane carboxylate (deltamethrin)
cyano(3-phenoxyphenyl)methyl ester of N-(2-chloro-4-trifluoromethylphenyl)alanine (Mavrik®).

The methods for making such compositions are well known. Solutions are prepared by simply mixing the ingredients. Fine solid compositions are made by blending and, usually, grinding as in a hammer or fluid energy mill. Suspensions are prepared by wet milling. Granules and pellets can be made by spraying the active material on preformed granular carriers or by agglomeration techniques.

Disease control is accomplished by applying the compounds of this invention to the portion of the plant to be protected. The compounds can be applied as preventive treatments prior to inoculation with the pathogen, or after-inoculation as a curative post-infection treatment.

Rates of application for compounds of this invention will be influenced by specific host plants, fungal pathogens, and many factors of the environment must be determined under use conditions. Foliage sprayed with concentrations ranging from 1 to 500 ppm of active ingredient can be protected from disease under suitable conditions.

The "% Control" in Table 1 was calculated according to this formula:

$$100 - \left[ \frac{\text{disease rating on treated plants}}{\text{disease rating on untreated plants}} \times 100 \right] = \text{percent control}$$

The benzopentathiepins of this invention have generic utility as intermediates in the preparation of substituted 1,2-benzenedithiols which are free of the 1,3- and 1,4-dithiol isomers. Such substituted 1,2-benzenedithiols are known intermediates to pharmaceuticals (U.S. Pat. No. 4,242,510; Sindelar et al., Collect. Czech. Chem. Comm., 47, 72 to 87 (1982), pesticides (U.S. Pat. No. 3,746,707), and rubber crosslinking agents (U.S. Pat. No. 3,979,369).

Reduction of the benzopentathiepins with, for example, sodium borohydride gives solutions of disodium benzene dithiolates which can be neutralized to give the dithiol or alkylated with methyl iodide to give 1,2-bis-(alkylthio)benzene derivatives. It would be possible to react the dithiolates with anhydrides; acid halides; esters; isocyanates; sulfonyl halides; tri- and pentavalent phosphorous esters, halides and anhydrides to make other useful materials.

In the following Examples the inert atmosphere was $N_2$. Kugelrohr distillation refers to a bulb-to-bulb microdistillation assembly. Examples 1 to 7 and 16 illustrate the process of the invention for preparation of benzopentathiepins. Examples 2 to 7 and 16 illustrate novel benzopentathiepins. Examples 8 to 10 illustrate the yield enhancement of the process by employing DABCO. Examples 11, 12 and 15 illustrate the novel benzothiadiazole compounds. Examples 13 and 14 illustrate the process for conversion of benzopentathiepins to dithiols. In both Examples 13 and 14, the dithiols obtained are isolated as bismethylthioethers to prevent aerobic oxidation. These bismethylthioethers can be converted back to the benzenedithiols by treatment with, for example, sodium in liquid ammonia.

EXAMPLE 1

Benzopentathiepin

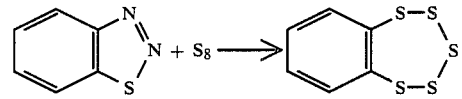

Sulfur (1.88 g, 7.3 mmol), 1,2,3-benzothiadiazole (1.0 g, 7.3 mmol) and Decalin®, i.e., decahydronaphthalene (10 mL) were combined and heated to 170° C. for 1.45 h. The resulting mixture was taken up in carbon disulfide and chromatographed on Silica Woelm®TSC (250 g, hexane). After a 340 mL forerun, 50 mL fractions were taken. Fractions 4 to 16 contained 1.61 L g of oily solid. This residue was triturated with hexane (30 mL) while methylene chloride (15 mL) was added slowly. Sulfur, 0.47 g was left as residue. The yellow solution was purified in 3×15 mL portions by medium pressure liquid chromatography (MPLC) (Lobar® Silica gel 60 size C, hexane) to give 0.60 g (34%) of benzopentathiepin as a light yellow solid, mp 56° to 58°

C. A sample recrystallized once from hexane had a mp of 58° to 60° C.; ¹H-NMR(CDCl₃, 90 MHz) δ 7.85–7.7 and 7.45–7.2 (AA'BB' multiplet) in agreement with the literature. The mass spectrum from a sample prepared similarly but not purified by MPLC had Mass spec.: m/e 235.8914; calcd m/e for C₆H₄S₅ 235.8917.

EXAMPLE 2

7-Chlorobenzopentathiepin

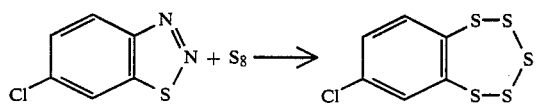

A mixture of sulfur (4.5 g, 17.6 mmol), 6-chloro-1,2,3-benzothiadiazole (3.0 g, 17.6 mmol) and Decalin ® (12 mL) was heated to 170° C. for 1 h and nitrogen evolved steadily. The mixture was then heated to 180° C. for 1 h. The solution was cooled and the solvent was removed in a stream of nitrogen overnight. The yellow residue was dissolved in carbon disulfide and absorbed onto Silica Woelm ®TSC (20 g) and chromatographed on 250 g of the same silica (hexane eluent). After a 300 mL forerun, sulfur and residual decalin were eluted in 100 mL, then 4.59 g of sulfur and product were obtained in 750 mL. A 0.3 g sample was partially dissolved in hexane (10 mL) with stirring and portionwise addition of methylene chloride (10 mL). After 10 min, 0.07 g sulfur was decanted. The solution was purified by medium pressure liquid chromatography (Lobar ®Silica gel 60, size C, hexane eluent) to give 0.07 g of 7-chlorobenzopentathiepin corresponding to a 22.5% yield. A 0.05 g sample was recrystallized from boiling hexane (20 mL concentrated to 5 mL, cooling and seeding) to give 40 mg of off-white solid, mp 87.5° to 89° C. A sample from a similar preparation had ¹H-NMR (CDCl₃, 80 MHz) δ 7.9–7.7 (d, 2H), 7.4–7.2 (m, 1H); IR (KBr) 1095, 822 cm⁻¹; Mass spec.: m/e 269.8517; m/e calcd for C₆H₃ClS₅ 269.8527.

Anal. Calcd for C₆H₃ClS₅: C, 26.61; H, 1.12, S, 59.19. Found: C, 26.84; H, 1.22; S, 65.7, 56.01, 56.79

The difference between the calculated and found values for sulfur was ascribed to a temporary difficulty with the analysis.

EXAMPLE 3

7-Trifluoromethylbenzopentathiepin

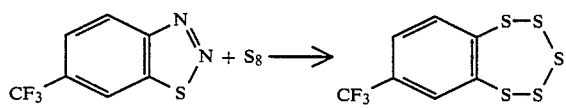

A mixture of sulfur (1.34 g, 4.9 mmol), 6-trifluoromethyl-1,2,3-benzothiadiazole (1.0 g, 4.9 mmol) and Decalin ® (10 mL) was heated to 190° C. for 45 min while nitrogen evolved. The mixture was cooled and stored overnight, then it was preadsorbed and chromatographed on Silica Woelm ®TSC (400 g, hexane) to give 1.36 g of a sulfur-product mixture. This mixture was triturated with hexane (40 mL), decanting from sulfur. The silution was purified by medium pressure liquid chromatography (Lobar ®Silica gel 60, size C) in 2 portions to give 0.46 g, 31% of 7-trifluoromethylbenzopentathiepin as a yellow oil which solidified on standing. A sample prepared by a similar procedure melted at 44° to 50° C. A sample recrystallized from hexane had mp 59° to 60° C.; ¹H-NMR (CDCl₃) δ 8.18 (d, J=2 Hz, 1H), 8.0 (d, J=8 Hz, 1H), 7.55 (dd, J=2, 8 Hz, 1H); IR(KBr) 1320 cm⁻¹; Mass spec.: m/e 303.8788; calcd m/e for C₇H₃F₃S₅ 303.8790.

Anal. calcd for C₇H₃F₃S₅: C, 27.62; H, 0.99; S, 52.66. Found: C, 27.92; H, 0.94; S, 51.75 C, 28.14; H, 1.10; S, 51.98

EXAMPLE 4

7-Dimethylaminobenzopentathiepin

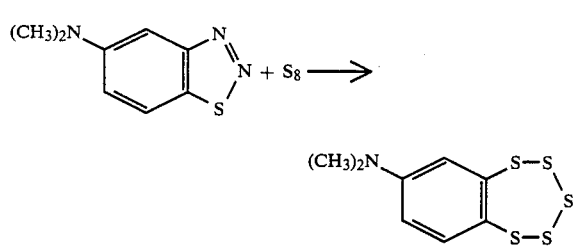

A mixture of sulfur (0.72 g, 2.79 mmol), 5-dimethylamino-1,2,3-benzothiadiazole (0.5 g, 2.79 mmol) and Decalin ® (5 mL) was heated to 170° C. for 1.5 h with steady evolution of nitrogen. The solution was cooled and the Decalin ® was removed by Kugelrohr distillation at 50° C. (0.3 mm). The residue was preadsorbed (5 g) and chromatographed (100 g) on Silica Woelm ®TSC (1% ether-hexane) giving first sulfur and then 0.32 g (40%) of 7-dimethylaminobenzo pentathiepin, mp 115° to 118° C.; ¹H-NMR (CDCl₃, 80 MHz) δ 7.55 (d, J=8.5 Hz, 1H), 7.0 (d, J=2.7 Hz, 1H), 6.5 (dd, J=8.5,2.7 Hz, 1H), 3.0 (s, 6H);

IR(KBr)1583 cm⁻¹; Mass spec.: m/e 278.9343, calcd m/e for C₈H₉NS₅ 278.9338. An 80 mg sample was recrystallized from boiling ethanol (50 mL filtered and concentrated to 20 mL) to give 70 mg of bright yellow crystals, mp 121.5° to 122.5° C.

Anal. calcd for C₈H₉NS₅: C, 34.38; H, 3.25; S, 57.36. Found: C, 34.21; H, 3.42; S, 56.99.

EXAMPLE 5

7-Methoxybenzopentathiepin

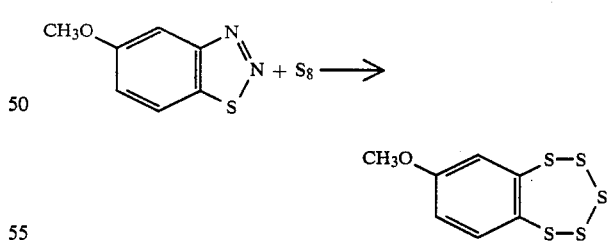

A mixture of sulfur (0.77 g, 3.01 mmol), 5-methoxy-1,2,3-benzothiadiazole (0.5 g, 3.01 mmol) and Decalin ® (5 mL) was heated to 170° C. for 1.5 h. The solution was cooled and the Decalin ® was removed by Kugelrohr distillation at 50° C. (0.3 mm). The residue was preadsorbed (5 g) and chromatographed (100 g) on Silica Woelm ®TSC (1% ether-hexane) to give first sulfur and then 0.27 g of 7-methoxybenzopentathiepin as a light yellow solid, mp 90° to 95° C. The sample was further purified by high pressure liquid chromatography (Zorbax ®Sil, 25% methylene chloride-hexane) to give 0.17 g, 21% of the product, mp 97° to 98° C.;

IR(KBr) 1577, 1291, 1229, 1037 cm$^{-1}$; Mass spec.: m/e 265.9011, m/e calcd for $C_7H_6OS_5$ 265.9002. A sample prepared by a similar procedure had $^1$H-NMR (CDCl$_3$, 80 MHz) δ 7.75 (d, J=8.3 Hz, 1H), 7.3 (d, J=2.7 Hz, 1H), 6.8 (dd, J=2.7, 8.3 Hz, 1H), 3.85 (s, 3H).

EXAMPLE 6

6-Bromobenzopentathiepin

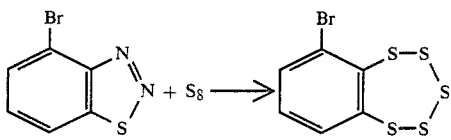

A mixture of sulfur (2.4 g, 9.3 mmol), 4-bromo-1,2,3-benzothiadiazole (2.0 g, 9.3 mmol) and Decalin® (20 mL) was heated to 175° C. for 1.25 h and nitrogen was evolved. The mixture was cooled and the solvent was removed by Kugelrohr distillation. The residue was preadsorbed and chromatographed (300 g) on Silica Woelm®TSC (1% ether-hexane) to give first sulfur and then 2.2 g of a sulfur-product mixture. The mixture was purified by high pressure liquid chromatography (Zorbax®Sil, hexane) to give 0.43 g, 14.6% of 6-bromobenzopentathiepin, retention time=5.12 min, mp 93° to 98° C.; IR(KBr) 788 cm$^{-1}$; Mass spec.: m/e 313.8036, m/e calcd for $C_6H_3BrS_5$ 313.8021.

A compound prepared similarly and recrystallized from hexane had a mp of 101° to 101.5° C.; NMR (CDCl$_3$, 360 MHz) δ 7.78 (dd, J=1.3, 8.0 Hz, 1H) 7.66 (dd, J=1.3, 8.0 Hz, 1H) 7.12 (t, J=8.0 Hz, 1H).

Anal. calcd for $C_6H_3BrS_5$: C=22.86; H=0.96. Found: C=23.53; H, 1.04. C=23.09; H, 0.94.

EXAMPLE 7

6-Trifluoromethylbenzopentathiepin

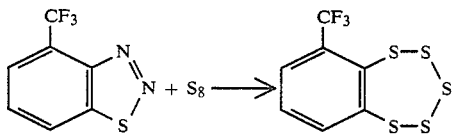

A mixture of sulfur (0.65 g, 2.45 mmol), 4-trifluoromethyl-1,2,3-benzothiadiazole (0.5 g, 2.45 mmol) and Decalin® (5 mL) was heated to 180° C. for 3 h and nitrogen was slowly evolved. The mixture was cooled and the solvent was removed by Kugelrohr distillation. The residue was preadsorbed and chromatographed (100 g) on Silica Woelm®TSC (1% ether-hexane) giving first sulfur and then 0.55 g of a sulfur-product mixture. The mixture was purified by high pressure liquid chomatography (Zorbax®Sil, hexane) to give 0.15 g, 20% of 6-trifluoromethylbenzopentathiepin as a light yellow solid, mp 55° to 60° C., retention time=5.26 min, IR(KBr) 1310, 1137, 1129, 1119 cm$^{-1}$; Mass spec.: m/e 303.8748, m/e calcd for $C_7H_3F_3S_5$ 303.8791. A compound prepared similarly and recrystallized from hexane had a mp of 61° to 62° C.

Anal. Calcd for $C_7H_3F_3S_5$: C=27.62; H=0.99. Found: C, 27.89; H, 1.06. C, 27.65;l H, 1.03.

EXAMPLE 8

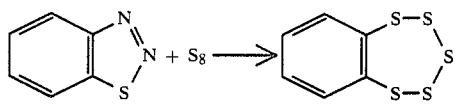

A mixture of sulfur (1.88 g, 7.3 mmol), 1,2,3-benzothiadiazole (1.0 g, 7.3 mmol), 1,4-diazabicyclo[2.2.2]octane (0.82 g, 7.3 mmol) and Decalin® (10 mL) was heated to 170° C. for 1.5 h while nitrogen was evolved. The mixture was cooled and the solvent was removed by Kugelrohr distillation. The residue was chromatographed on Silica Woelm®TSC (200 g, 1% ether-hexane). The fraction containing the product was further purified by high pressure liquid chromatography to give 0.94 g, 54%, of benzopentathiepin.

EXAMPLE 9

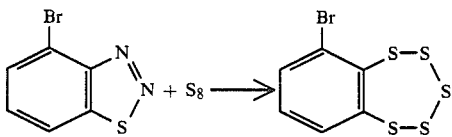

A mixture of sulfur (1.2 g, 4.65 mmol), 4-bromo-1,2,3-benzothiadiazole (1.0 g, 4.65 mmol), 1,4-diazacyclo[2.2.-2]octane (0.52 g, 4.65 mmol), and Decalin® (10 mL) was heated at 170° C. for 1.25 h. The mixture was cooled and the solvent was removed by Kugelrohr distillation. The residue was chromatographed on Silica Woelm®TSC (200 g, 1% ether-hexane). The fraction containing a sulfur-product mixture was further purified by high pressure liquid chromatography (Zorbax®Sil, hexane) to give 0.33 g, 22.6%, of 6-bromobenzopentathiepin.

EXAMPLE 10

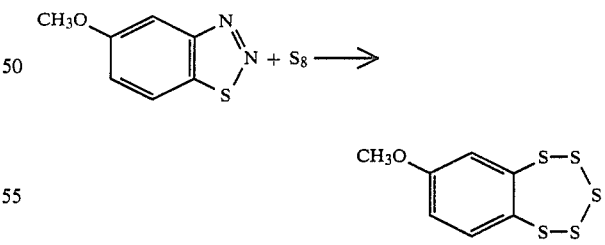

A mixture of sulfur (0.77 g, 3.01 mmol), 5-methoxy-1,2,3-benzothiadiazole (0.5 g, 3.01 mmol), 1,4-diazabicyclo[2.2.2]octane (0.34 g, 3.01 mmol) and Decalin® (5 mL) was heated to 170° C. for 1.25 h. The mixture was cooled and the solvent was removed by Kugelrohr distillation. The residue was chromatographed on Silica Woelm®TSC (200 g, 1% ether-hexane) to give first sulfur and then 0.46 g, 57%, of 7-methoxybenzopentathiepin.

EXAMPLE 11

4-Trifluoromethyl-1,2,3-Benzothiadiazole

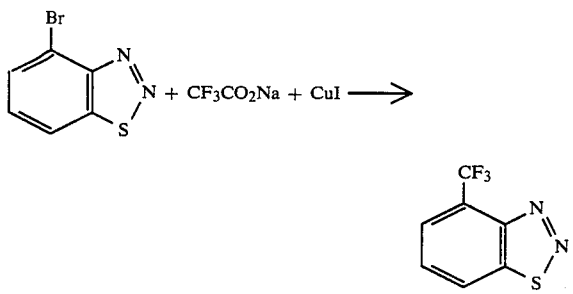

First, 4-bromo-1,2,3-benzothiadiazole (5.0 g, 23.2 mmol) was dissolved in N-methylpyrrolidinone (200 mL) and then sodium trifluoroacetate (8.5 g, 62.5 mmol) and cuprous iodide (8.75 g, 46 mmol) were added. The mixture was heated to 160° C. for 4 h (gentle $CO_2$ evolution), cooled, and diluted carefully with water (300 mL). The slurry was filtered through Celite ®️ (diatomaceous earth) and the pad was rinsed with ether (3×250 mL). The filtrate phases were separated and the organic layer was washed with water and brine; then it was filtered through a cone of calcium sulfate and concentrated. The crude product was chromatographed on Silica Woelm ®️TSC (500 g, 15% ether-hexane) to give first a mixture of 4-bromo and 4-iodo and 4-trifluoromethyl-1,2,3-benzothiadiazoles followed by pure 4-trifluoromethyl-1,2,3-benzothiadiazole. The mixed fraction was rechromatographed on the same column to give additional pure product. In this manner, 3.19 g, 67%, of 4-trifluoromethyl-1,2,3-benzothiadiazole was obtained as an off-white solid. A sample prepared by a similar procedure had mp 41° to 44° C.; $^{19}F$ NMR ($CDCl_3$) −58.78 (s). A sample further purified by sublimation at 45° C. (35–50 mm-water aspirator) had mp 49° to 51° C.; $^1H$-NMR ($CDCl_3$) δ 8.35 (d, J=8 Hz, 1H), 8.0 (d, J=8 Hz, 1H), 7.8 (t, J=8 Hz, 1H); IR(KBr) 1319, 1152, 1122, 1089 $cm^{-1}$.

Anal. calcd for $C_7H_3F_3N_2S$: C, 41.18; H, 1.48; N, 13.72. Found: C, 41.13; H, 1.37; N, 13.96.

EXAMPLE 12

6-Trifluoromethyl-1,2,3-Benzothiadiazole

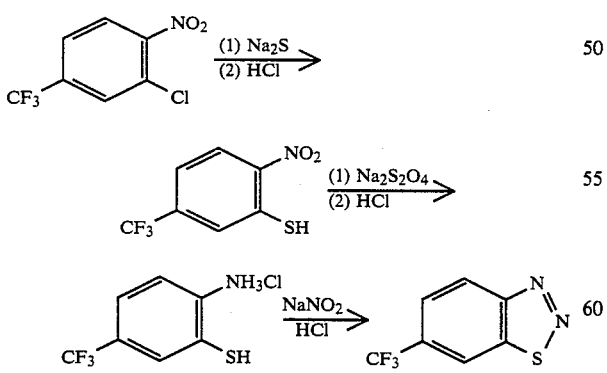

First, 2-chloro-4-trifluoromethylnitrobenzene (20 g, 88.6 mmol) was dissolved in dimethylsulfoxide (100 mL, dried over molecular sieves) under a nitrogen atmosphere and then anhydrous sodium sulfide (6.92 g, 88.6 mmol) was added all at once. The mixture warmed to about 40° C. and was stirred for 2 h. The red mixture was poured into a solution of brine (300 mL) and 6N HCl (100 mL) and extracted with methylene chloride (3×100 mL). The combined organic phase was filtered through a cone of sodium sulfate and concentrated to leave 18.46 g of yellow solid.

Nitrogen was bubbled through deionized water (400 mL) for 15 min, then the above yellow solid and ammonium hydroxide (90 mL) were added. Sodium hydrosulfite (90 g) was dissolved in deionized water (400 mL) and added to the mechanically stirred reaction over 10 to 15 min via an addition funnel. The resulting solution was warmed to 50° C. for 3 h, then stirred overnight at ambient temperature. The mixture was acidified to pH 7 with acetic acid and extracted with ether (3×200 mL). The combined organic layer was washed with brine and filtered through a cone of calcium sulfate into a flask equipped with mechanical stirring and a gas inlet. Hydrogen chloride was bubbled through the stirred solution for 1.5 h. The solid was filtered, rinsed with dry ether and dried in vacuo to give 8.96 g of hydrochloride salt, mp 184° to 188° C.; IR (KBr) 1330 $cm^{-1}$.

The above salt was slurried in 5% aqueous HCl (100 mL) and chilled to 0° C. A solution of sodium nitrite (3.22 g) in water (15 mL) was added dropwise over 20 min to the stirred mixture; then it was neutralized to pH 9 with 20% aqueous sodium hydroxide. The reaction was extracted with ether (3×100 mL) and the organic phase was washed with water and brine and then filtered through a cone of sodium sulfate. Concentration left 6.94 g of a brown oil which was chromatographed on Silica Woelm ®️TSC (250 g, 10% ether-hexane) to give (after a 350 mL forerun) a trace of impurity in 250 mL and then 2.35 g of 6-trifluoromethyl-1,2,3-benzothiadiazole in 150 mL of eluent. A sample sublimed at 25° C. (0.15 mm) had mp 36° to 40° C.; $^1H$-NMR ($CDCl_3$, 90 MHz) δ 8.9 (m, 1H), 8.25 (dd, 1H), 7.9 (ddd, 1H); IR (KBr) 1332, 1294, 1192, 1150, (sh) 1129 $cm^{-1}$. A sample prepared by a similar procedure had mp 40° to 42° C.

| Anal. calcd for $C_7H_3F_3N_2S$: | C, 41.18; | H, 1.48; | N, 13.72. |
|---|---|---|---|
| Found: | C, 41.31; | H, 1.51; | N, 13.56. |
| | 40.95 | 1.73 | 13.82. |

EXAMPLE 13

3,4-Bis(methylthio)-N-N-dimethylaniline

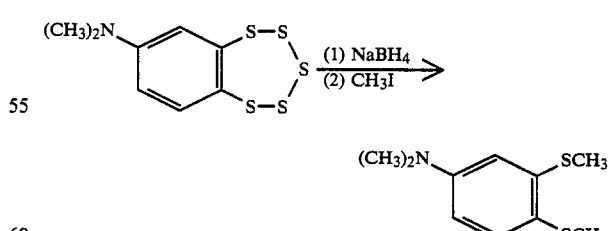

This Example illustrates the making of a compound useful (as the unprotected dithiol) as a rubber cross-linking agent. First, 7-dimethylaminobenzopentathiepin (0.5 g, 1.79 mmol) was dissolved in tetrahydrofuran (50 mL) and ethanol (50 mL) was added. Sodium borohydride (0.34 g, 8.96 mmol) was added to the stirred solution at ambient temperature over 5 min (after a short induction time hydrogen gas was evolved and the solution warmed slightly). When the foaming ceased in about 15 min, water (10 mL) was added and the mixture was warmed to 50° C. for 5 min followed by cooling to ambient temperature and addition of methyl iodide (0.62 mL, 10 mmol). After stirring 30 min more, the solvent was removed and the residue was partitioned between water and ether. The phases were separated and the organic phase was washed with brine and dried through a cone of sodium sulfate. Concentration gave a yellow oil which was chromatographed on Silica Woelm ®TSC (50 g, 20% ether-hexane) to give 0.33 g, 86%, of 3,4-bis(methylthio)-N,N-dimethylaniline as a yellow oil which crystallized on standing, mp 49° to 51° C.;

IR (neat) 1583 cm$^{-1}$; $^1$H-NMR (CDCl$_3$, 80 MHz) δ 7.22 (d, J=9.3 Hz, 1H), 6.49 (d, partially obscured, J=2.9 Hz, 1H), 6.4 (dd, partially obscured, J=2.9, 9.3 Hz, 1H), 2.95 (s, 6H), 2.46 (s, 3H), 2.38 (s, 3H).

Anal. calcd for C$_{10}$H$_{15}$NS$_2$: C, 56.30; H, 7.09. Found: C, 56.69; H, 6.93. C, 56.72; H, 6.96.

EXAMPLE 14

3,4-Bis(methylthio)-chlorobenzene

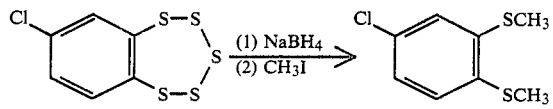

This Example illustrates the making of a compound useful as an intermediate (as the unprotected dithiol) to a tricyclic psychotropic agent. First, 7-chlorobenzopentathiepin (0.32 g, 1.18 mmol) was dissolved in tetrahydrofuran (30 mL) and ethanol (30 mL) was added. Sodium borohydride (0.22 g, 5.91 mmol) was added over 5 min in portions at ambient temperature causing the solution to evolve hydrogen gas and warm slightly. After gas evolution had ceased in about 15 min, water (10 mL) was added and the mixture was heated to about 50° C. for 5 min and cooled to ambient temperature. Methyl iodide (0.44 mL, 7.0 mmol) was added and the solution was stirred. The solvents were removed and the residue was partitioned between ether and water. The phases were separated and the organic layer was washed with brine and dried through a cone of sodium sulfate. Concentration left an oil which was chromatographed on Silica Woelm ®TSC (50 g, 10% ether-hexane) to give 0.16 g, 67%, of 3,4-bis(methylthio)chlorobenzene as a clear pale yellow oil; $^1$H-NMR (CDCl$_3$, 90 MHz) δ 7.1 (s, 3H), 2.46 (s, 3H), 2.44 (s, 3H), 1.4 (small impurity); IR (neat) 1448, 1430, 1029, 801 cm$^{-1}$;

Mass spec.: m/e 203.9852, m/e calcd for C$_8$H$_9$ClS$_2$ 203.9834.

EXAMPLE 15

4,5-Bis(dimethylamino)-1,2,3-benzothiadiazole

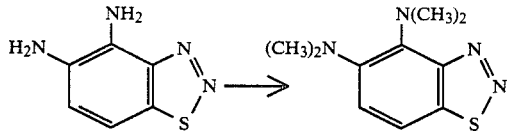

A 3 necked round bottom flask fitted with magnetic stirrer, condenser, static nitrogen atmosphere and a septum was charged with sodium hydride (0.35 g, 50% mineral oil dispersion, 7.2 mmol). The oil was rinsed away with dry hexane (3 times using standard syringe technique) then dry tetrahydrofuran (20 mL) was added. To the slurry was added 4,5-diamino-1,2,3-benzothiadiazole (0.2 g, 1.2 mmol) neat over 5 min. Finally, methyl iodide (0.75 mL, 12 mmol) was added and the mixture was stirred at ambient temperature for 72 h. The mixture was cautiously quenched with water, the solvent was stripped off, and methylene chloride was added to the residue. After extraction of this organic phase with water and brine, it was filtered through a cone of sodium sulfate and concentrated onto silica gel. Chromatography on silica gel (5% ether-hexane) gave 0.11 g (41%) of 4,5-bis(dimethylamino)-1,2,3-benzothiadiazole as an orange oil: NMR (90 MHZ) δ 7.38 (ABq Δν$_{1-3}$=18 Hz, J=8 Hz, 2H), 3.26 (s, 6H), 2.8 (s, 6H); IR (neat) 2980–2780 (multiplet, m) 1542, 1495 cm$^{-1}$; exact mass calcd for C$_{10}$H$_{14}$N$_4$S; M/e 222.0939, observed M/e 222.0950.

EXAMPLE 16

6,7-Bis(dimethylamino)benzopentathiepin

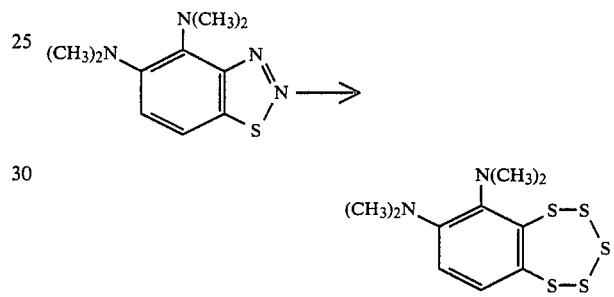

A magnetically stirred mixture of 4,5-bis(dimethylamino)-1,2,3-benzothiadiazole (2.0 g, 9.0 mmol), sulfur (2.3 g, 9.0 mmol) and decalin (30 mL) was heated to 175° C. under a static nitrogen atmosphere for 1.5 h. During this time, nitrogen-evolution was steady. The mixture was cooled to ambient temperature and the decalin was removed by kugelrohr distillation. The residue was chromatographed on silica gel (1% ether-hexane) to give 2.04 g (70%) of 6,7-bis(dimethylamino)-benzopentathiepin. A 1 g sample was recrystallized from 100 mL of hexane by chilling to −78° C. to give 0.7 g of bright orange solid: mp 59.5° to 61° C. Anal. Calcd for C$_{10}$H$_{14}$N$_2$S$_5$; C, 37.24; H, 4.38; Found: C, 37.45; H, 4.66. A sample prepared by a similar procedure had: NMR (80 mHz) δ 7.15 (ABq Δν$_{1-3}$=59 Hz, J=8.5 Hz, 2H), 2.9 (s, 6H), 2.8 (s, 6H).

The embodiments of the invention in which an exclusive property or privilege is claimed are defined as follows:

1. A benzopentathiepin compound of the formula

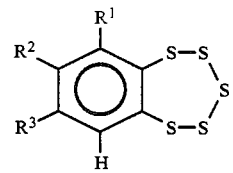

wherein

R$^1$, R$^2$, and R$^3$ are the same or different and are selected from H (provided that no more than two of $R^1$, $R^2$, and $R^3$ are H), X, $CX_3$, $NO_2$, $SR^4$, $OR^4$, $NR^4_2$,

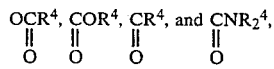

$R^4$ is selected from substituted and unsubstituted branched or straight chain $C_1$ to $C_6$ alkyl, wherein the substituents on substituted $R^4$ alkyl groups are selected from X, $CX_3$, OR, SR,

and COOR, wherein R is $C_1$ to $C_4$ straight or branched alkyl; and

X is selected from Cl, Br, and F.

2. A compound according to claim 1 wherein $R^1$ and $R^3$ are both H and $R^2$ is selected from X, $CX_3$, $SR^4$, $OR^4$, $NR^4_2$, and $COOR^4$.

3. A compound according to claim 2 wherein $R^2$ is selected from $N(CH_3)_2$, $OCH_3$, $CF_3$, and Cl.

4. A compound according to claim 1 wherein $R^2$ and $R^3$ are both H and $R^1$ is selected from X, $CX_3$, $SR^4$, $OR^4$, $NR^4_2$, and $COOR^4$.

5. A compound according to claim 4 wherein $R^1$ is selected from $CF_3$ and Br.

6. A compound according to claim 3, 7-trifluoromethylbenzopentathiepin.

7. A compound according to claim 3, 7-dimethylaminobenzopentathiepin.

8. A compound according to claim 3, 7-methoxybenzopentathiepin.

9. A compound according to claim 5, 6-trifluoromethylbenzopentathiepin.

10. A compound according to claim 3, 7-chlorobenzopentathiepin.

11. A compound according to claim 5, 6-bromobenzopentathiepin.

12. A compound according to claim 1 wherein $R^1$ and $R^2$ are both $NR^4_2$ and $R^3$ is H.

13. A compound according to claim 12 wherein $R^4$ is methyl.

14. An anti-fungal formulation comprising an effective amount of a compound according to claim 1.

15. A formulation according to claim 14 wherein the compound is
7-trifluoromethylbenzopentathiepin.

16. A formulation according to claim 14 wherein the compound is
7-dimethylaminobenzopentathiepin.

17. A formulation according to claim 14 wherein the compound is 7-methoxybenzopentathiepin.

18. A formulation according to claim 14 wherein the compound is
6-trifluoromethylbenzopentathiepin.

19. An anti-viral formulation comprising an effective amount of a compound according to claim 1.

20. A formulation according to claim 19 wherein the compound is
7-dimethylaminobenzopentathiepin.

* * * * *